"" (12) United States Patent
Kinoshita

(10) Patent No.: US 7,588,366 B2
(45) Date of Patent: Sep. 15, 2009

(54) HEAT FLOW FLUX TYPE DIFFERENTIAL SCANNING CALORIMETER

(75) Inventor: Ryoichi Kinoshita, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 0 days.

(21) Appl. No.: 12/031,283

(22) Filed: Feb. 14, 2008

(65) Prior Publication Data

US 2008/0187020 A1      Aug. 7, 2008

Related U.S. Application Data

(63) Continuation of application No. PCT/JP2006/316445, filed on Aug. 23, 2006.

(30) Foreign Application Priority Data

Sep. 1, 2005    (JP) .................. 2005-253704

(51) Int. Cl.
*G01K 17/00* (2006.01)
*G01K 7/00* (2006.01)
*G01N 25/00* (2006.01)

(52) U.S. Cl. ................... 374/12; 374/29; 374/30; 374/31; 374/43; 374/112

(58) Field of Classification Search ............. 422/51; 374/10, 12, 31, 29, 30, 43, 112
See application file for complete search history.

(56) References Cited

U.S. PATENT DOCUMENTS

| 7,371,006 | B2 * | 5/2008 | Schick | 374/10 |
| 2004/0001524 | A1 * | 1/2004 | Jorimann et al. | 374/10 |
| 2005/0190813 | A1 * | 9/2005 | Schick | 374/10 |
| 2006/0187998 | A1 * | 8/2006 | Danley | 374/10 |

FOREIGN PATENT DOCUMENTS

| JP | 56082436 A | * | 7/1981 |
| JP | 59-153156 A | | 9/1984 |
| JP | 60-64250 U | | 5/1985 |
| JP | 63255649 A | * | 10/1988 |
| JP | 4-348264 A | | 12/1992 |
| JP | 7-92117 A | | 4/1995 |
| JP | 2000-28559 A | | 1/2000 |
| JP | 2003-42985 A | | 2/2003 |

OTHER PUBLICATIONS

International Search Report issued Nov. 21, 2006.

* cited by examiner

*Primary Examiner*—Gail Verbitsky
*Assistant Examiner*—Mirellys Jagan
(74) *Attorney, Agent, or Firm*—Brinks Hofer Gilson & Lione

(57) ABSTRACT

There is provided a differential scanning calorimeter in which a base line stability and a responsiveness are improved. There is made a constitution in which the stability is ensured by making a neck-like part in a heat passage from a heat reservoir 1 to a sensor plate 4 and, at the same time, a two-dimension heat flow passage to a sample holder 5a is ensured.

12 Claims, 4 Drawing Sheets

SAMPLE HOLDER TEMPERATURE-SIGNAL OUTPUT

DIFFERENTIAL HEAT FLOW SIGNAL OUTPUT

HEAT FLOW FLUX TYPE DIFFERENTIAL SCANNING CALORIMETER

This application is a continuation of PCT/JP2006/316445, filed Aug. 23, 2006, which claims priority to Japanese Application No. JP2005-253704, filed Sep. 1, 2005. The entire contents of these applications are incorporated herein by reference.

TECHNICAL FIELD

The present invention relates to a thermal analysis apparatus measuring how a physical or chemical nature of a sample changes in accordance with a temperature, and especially a heat flow flux type differential scanning calorimeter measuring, on the basis of a temperature difference (differential heat) between the sample and a reference material, a differential heat flow that the sample excessively generates or absorbs in comparison with the reference material when the temperature is changed at a constant velocity.

BACKGROUND ART

The differential scanning calorimeter is an apparatus in which the sample and the reference material (which is a thermally stable reference material, and aluminum or the like is ordinarily used) are symmetrically disposed, and a heat flow that the sample excessively generates or absorbs in comparison with the reference material when temperatures of both are changed at a constant velocity is differentially detected and analyzed.

In a case where the temperature of the sample is raised at the constant velocity, a heat absorption by the sample increases as a heat capacity of the sample becomes large. That is, an absolute value of a differential heat flow signal becomes large. At this time, from the fact that the absolute value of the differential heat flow signal is proportional to a heat capacity difference between the sample and the reference material, and a temperature raising velocity, it is possible to know the heat capacity of the sample from the differential heat flow signal on the basis of the temperature raising velocity and a reference heat capacity, which are already known.

On the other hand, when the sample melts, a heat absorption by the sample becomes temporarily large and, if the differential heat flow signal recorded in time series is made a graph, the differential heat flow signal depicts an endothermic peak. Further, according to a similar recording method, if a crystallization occurs in the sample, the differential heat flow signal depicts an exothermic peak. Since areas of these endothermic and exothermic peaks depicted in regard to a time axis set such that a unit time corresponds to a constant length are proportional to a heat quantity (transition heat) that the sample discharges or absorbs when it transfers, if a known transition heat is previously measured and a signal value is calibrated, it is possible to easily find the transition heat of the sample from the differential heat flow signal. In order to obtain the differential heat flow signal having a useful nature like the above, the differential scanning calorimeter is widely used in analyses of various materials.

Hitherto, as the differential scanning calorimeter of this kind, there are ones shown in FIG. 5, FIG. 6 and FIG. 7.

FIG. 5 is one disclosed in JP-A-2003-42985 Gazette, in which a heat flows from a convex protrusion part 1 provided in a bottom part center of a heat reservoir to a sample side holder 3 and a reference side holder 4 through a long-plate-like heat flow passage 2 made of a metal material, and a temperature difference is detected by thermocouples installed in back faces of the respective holders. Additionally, in this example, for the purpose of raising a heat flow responsiveness (heat compensation time constant is decreased), a heater for compensating an input is provided in a holder part, thereby making a constitution of an input compensation type DSC.

FIG. 6 is disclosed in JP-UM-A-60-64250 Gazette, and a form is provided in which a detector is directly mounted on a bottom plate of a heating furnace comprising a good heat conductor, whose section is like an H-letter, a temperature distribution is suppressed by providing a neck-like part in a heat flow passage in the detector, and a heat one-dimensionally flows into a sample part and a reference part.

FIG. 7 is one disclosed in JP-A-2000-28559 Gazette, and a structure is provided in which, in order to improve the heat flow responsiveness, a sensor, in which a heat flow passage 3 is two-dimensionally disposed, is installed on a heat reservoir bottom plate through a heat buffer plate 6 formed by a low thermal conduction material.

SUMMARY OF THE INVENTION

Problems that the Invention is to Solve

In a structure of FIG. 6 disclosed in the Patent Document 2, although there is an advantage suppressing the temperature distribution by providing the neck-like part in the heat flow passage and a stability of a base line is obtained, since it is a form in which a heat one-dimensionally flows into the sample part and the reference part, it is difficult to decrease a heat resistance of the heat flow passage, so that there is a drawback that it is inferior in the heat flow responsiveness.

Also in the example of FIG. 5 disclosed in the Patent Document 1, in order to obtain the stability of the base line, by a structure in which the heat flows from the convex protrusion part 1a provided in the bottom part center of the heat reservoir to the sample side holder 3 and the reference side holder 4 through the long-plate-like heat flow passage 2, the neck-like part is provided in the heat flow passage to thereby suppress the temperature distribution and, at the same time in order to raise the heat flow responsiveness, the heater for compensating the input is provided in the holder part, thereby making the constitution of the input compensation type DSC. However, since the input compensation heater for raising the heat flow responsiveness and a feedback circuit are provided, there is a drawback that an apparatus constitution becomes complicated.

Although the structure of FIG. 7 disclosed in the Patent Document 3 is the structure in which the sensor, in which the heat flow passage 3 is two-dimensionally disposed in order to improve the heat flow responsiveness, is installed on the heat reservoir bottom plate through the heat buffer plate 6 formed by the low thermal conduction material, since heat inflow paths to a holder part enter from all directions of a holder outer circumference, an influence of the temperature distribution cannot be excluded completely, so that there is a drawback that the stability of the base line is difficult to be obtained.

Means for Solving the Problems

Following means are used in order to provide a heat flow flux type differential scanning calorimeter in which there is provided the neck-like part, of a heat reservoir heat flow passage, easy to obtain the stability of the base line and, at the same time, there is formed a two-dimensional heat flow passage for improving the heat flow responsiveness, and which has no complicated constitution such as input compensation heater. There is made a structure in which holders for mounting the sample and the reference material are provided in major axis direction both-end vicinities of an oval-like metal plate, a sensor plate is made by welding a thermocouple for a temperature detection to each holder back face, the sensor plate is nipped by the convex protrusion part provided near a bottom part center of a heat reservoir comprising a good heat conductor with a bottom plate, which has a cylindrical inside space and a good heat conductor presser plate of approximately the same as the former such that the respective holders of the sample and the reference material become symmetrical to an oval minor axis, the convex protrusion part is made the neck-like part of the heat reservoir heat flow passage to thereby make it a heat inflow port to the sensor plate, and a heat flow passage from a boundary line of the sensor plate nipped by the convex protrusion part to the holder is made a two-dimension heat flow passage.

Actions by this structure are as follows. There is reduced the temperature distribution, in a heat reservoir radial direction, of the heat flow flowing into the sensor plate by the neck-like part of the heat reservoir heat flow passage and, at the same time, the two-dimension heat flow passage to the sample holder performs a rapid heat compensation response to a heat change of the sample.

Advantage of the Invention

Like the above, in the heat flow flux type differential scanning calorimeter, by the facts that there is made the constitution in which the stability is ensured by making the neck-like part in the heat flow passage from the heat reservoir to the sensor plate and, at the same time, there is ensured the two-dimension heat flow passage to the sample holder, there is an advantage that there can be realized a stability improvement of the base line, at the same time, a heat flow flux type differential scanning calorimeter having a rapid heat compensation responsiveness without using the input compensation heater or a compensation circuit.

DETAILED DESCRIPTION OF THE PREFERRED EMBODIMENTS

Best Mode for Carrying Out the Invention

Hereunder, a first implementation mode of a heat flow flux type differential scanning calorimeter concerned with the present invention is explained by referring to FIG. 1 to FIG. 4.

Figure 1:
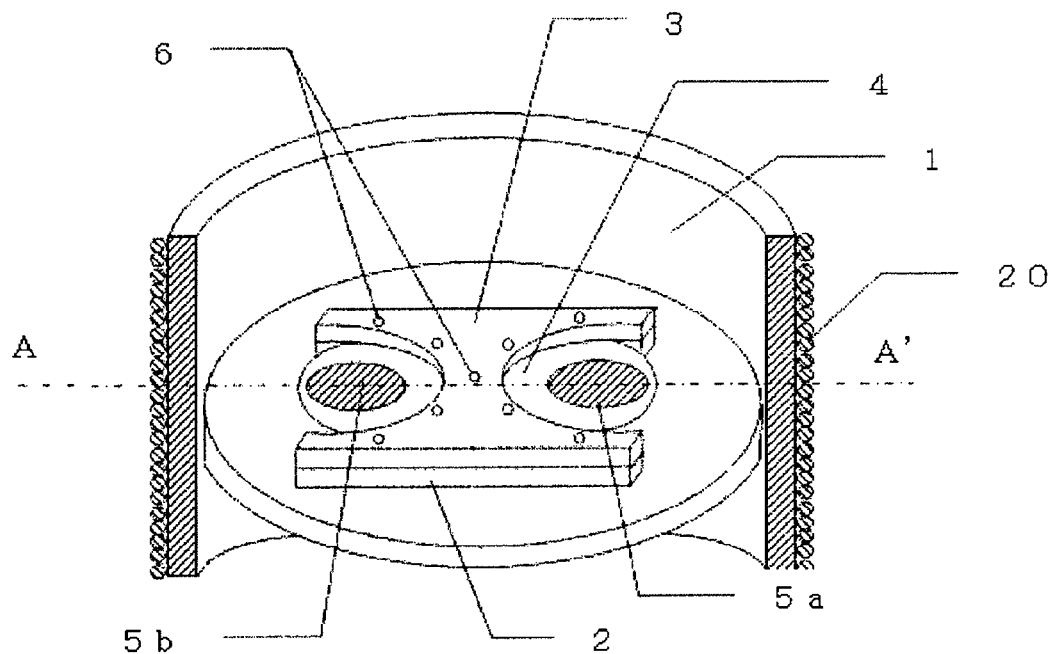
FIG. 1 is a constitutional view including a partial sectional view, which shows one embodiment of the present invention.
Figure 2:
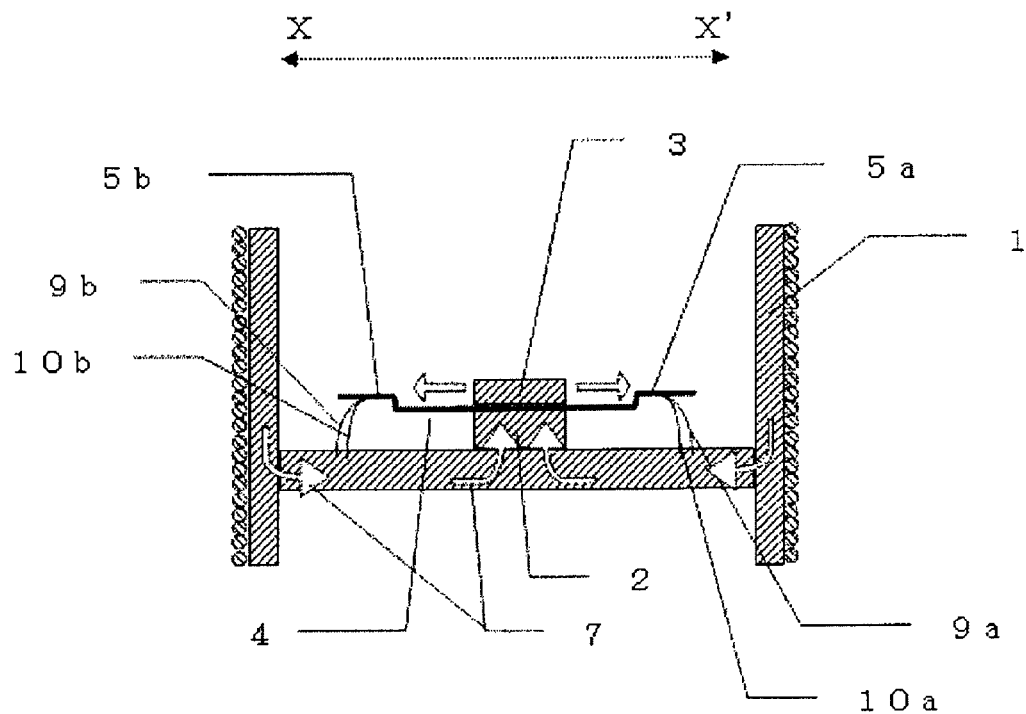
FIG. 2 is an A-A' sectional view of FIG. 1.
Figure 3:
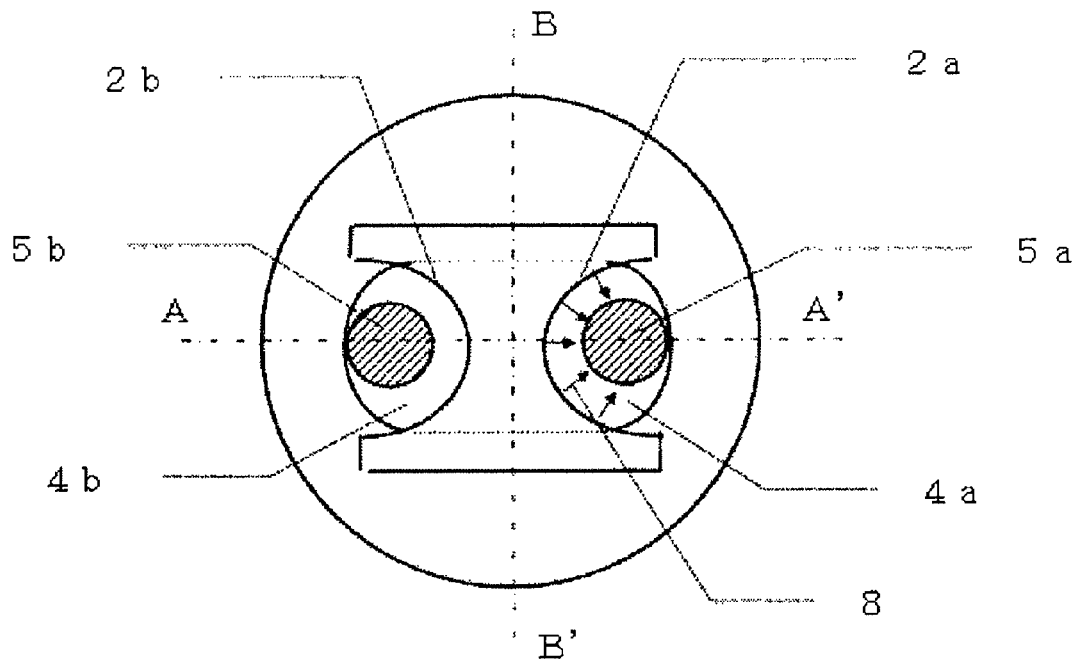
FIG. 3 is a view in which a sensor structure of the present embodiment is seen from above, and a top view of FIG. 1.
Figure 4:
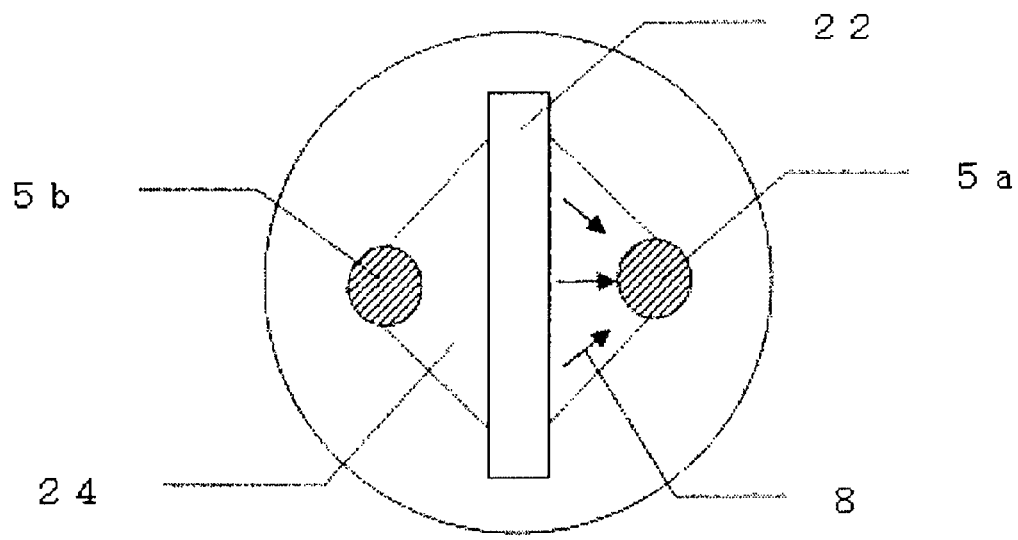
FIG. 4 is a view showing a different embodiment of the present invention.
Figures 5, 6:
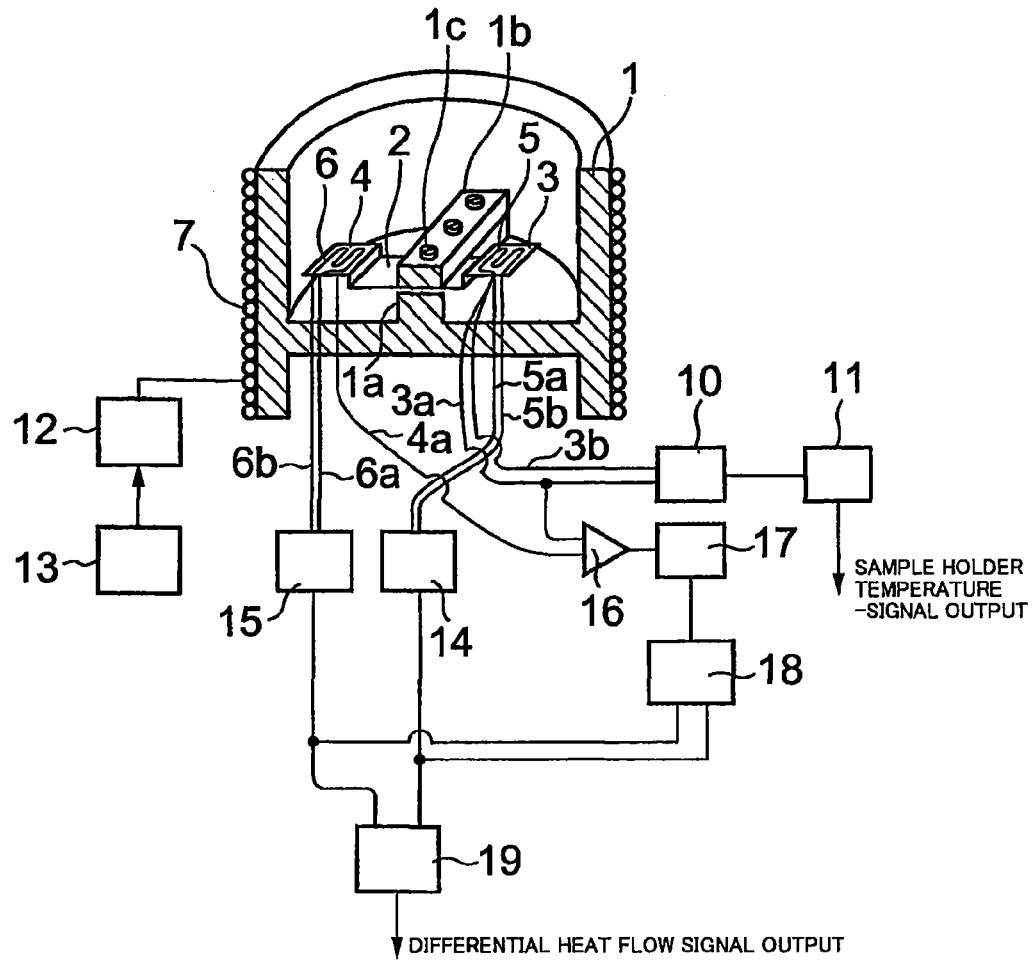
FIG. 5 is a conventional example disclosed in JP-A-2003-42985 Gazette.
FIG. 6 is a conventional example disclosed in JP-UM-A-60-64250 Gazette.
Figure 7:
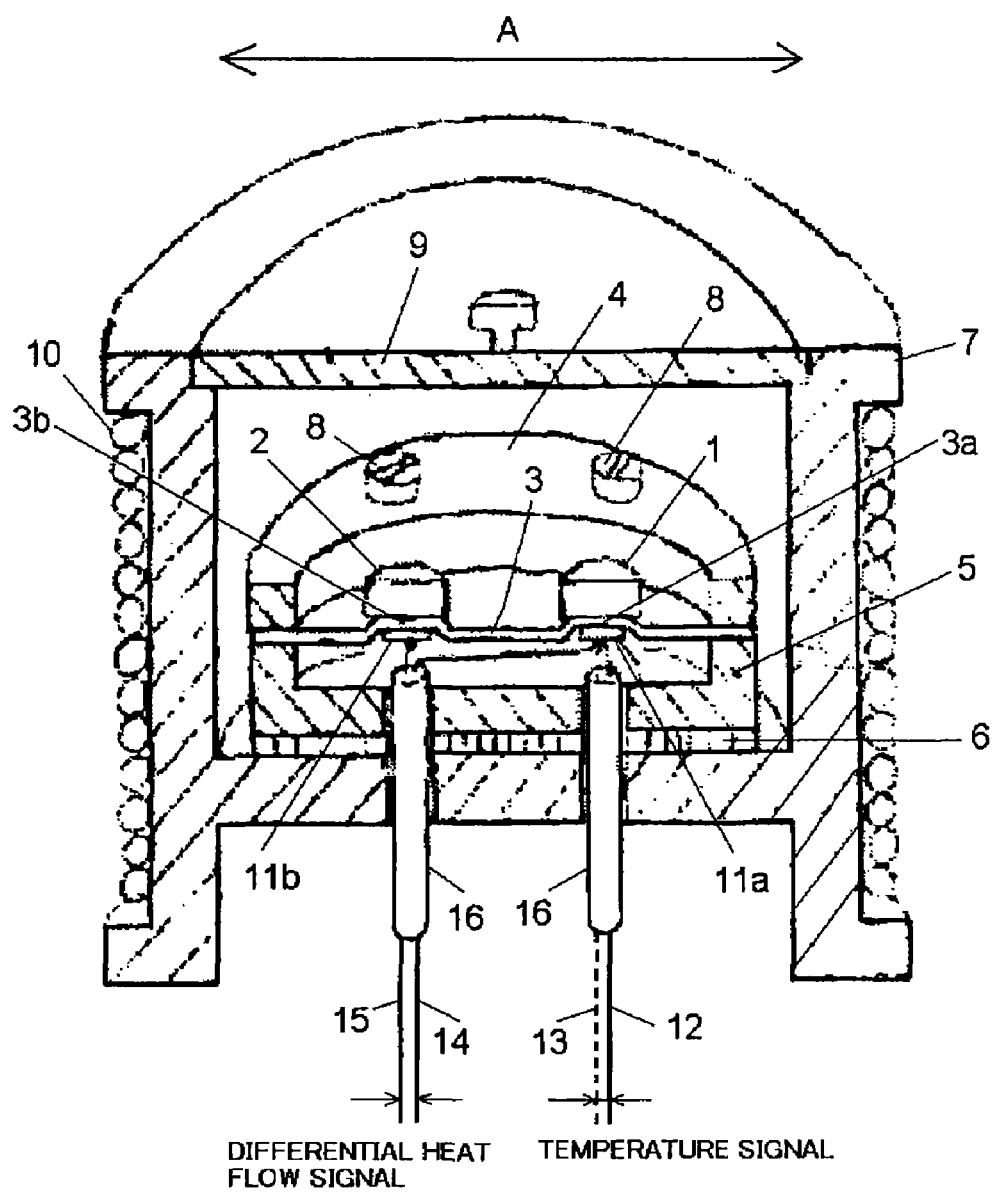
FIG. 7 is a conventional example disclosed in JP-A-2000-28559 Gazette.

FIG. 1 is a view showing constitutions of a heat reservoir and a sensor plate in the differential scanning calorimeter according to the present invention, and only a cylindrical portion of the heat reservoir is shown by a sectional view such that a structure is easy to be understood. FIG. 2 shows an A-A' sectional view of FIG. 1. FIG. 3 is a view in which a sensor structure is seen from above, and shows a top view of FIG. 1.

1 is a heat reservoir made of silver which is a good heat conductor and, around its outer circumference, there is wound a heater 20 for a temperature control, which is insulation-coated. As understood from the A-A' sectional view of FIG. 2, the heat reservoir 1 is like a cylinder, its section forms an approximately H-letter shape and, in its bottom part center, there is formed a convex protrusion part 2. As seen in the top view of FIG. 3, the protrusion part 2 is a shape symmetrical to both of an A-A' axis and a B-B' axis perpendicular to the former, and has semicircular arc parts 2a, 2b mutually facing on the A-A' axis. 4 is an oval-like sensor plate made of a suitable metal material (constantan is used in the embodiment) whose thermal conductivity is lower than the silver which is a material of the heat reservoir 1. A sensor plate center part is nipped between an upper face of the convex protrusion part 2 in the bottom part center of the heat reservoir 1 and a presser plate 3 made of the silver, which is approximately the same shape as the protrusion part 2, and fixed, together with the presser plate 3, to the upper face of the convex protrusion part 2 in the bottom part center of the heat reservoir 1 by plural screws 6. Additionally, both-tip vicinities on a major axis (A-A' axis) of the sensor plate 4 make face-like regions bulged like a platform, and gold discs are welded to here, thereby constituting respectively a sample holder 5a and a reference material holder 5b. The sample holder 5a and the reference material holder 5b are disposed symmetrically to a B-B' axis in FIG. 3. In the present embodiment, as a constitution of the sample holder, although the gold disc is welded, if it is one of a shape capable of performing a good thermal contact with a sample container to be mounted, by a material having a thermal conductivity equivalent to or higher than the sensor plate, it is self-evident that it can be constituted as the sample holder.

Further, even if the sensor plate is not lifted up like the platform, if a metal plate, whose thermal conduction is good, or the like is fixed by a welding or the like, it functions as the sample holder. As a material, instead of the gold, there may be used a platinum plate or a silver plate. Also as to a fixation to the sensor plate, it may be a brazing or the like, besides the welding.

Additionally, the sensor plate itself may be merely made like the platform. On the other hand, as seen in FIG. 3, the semicircular arc parts 2a and 2b on the A-A' axis of the protrusion part 2 and the presser plate 3 become shapes surrounding approximately, concentrically in regard to the sample holder 5a and the reference material holder 5b, respectively. These semicircular arc parts 2a and 2b of the protrusion part 2 form, as one part of the heat reservoir, heat inflow ports in regard to the sample holder 5a and the reference material holder 5b. By this, the sensor plate 4a between the semicircular arc part 2a and the sample holder 5a, and the sensor plate 4b between the semicircular arc part 2b and the reference material holder 5b form respectively two-dimension heat flow paths to the sample holder 5a and the reference material holder 5b.

A chromel wire 9a and an alumel wire 10a are welded to a back face of the sample holder 5a, and a chromel wire 9b and an alumel wire 10b are welded to a back face of the reference material holder 5b. In the sample holder 5a back face and the reference material holder 5b back face, there exist respectively chromel-constantan junctions, and the sample holder 5a and the reference material holder 5b are connected by the sensor plate 4. Accordingly, a connection among the chromel wire 9a, the sample holder 5a, the sensor plate 4, the reference material holder 5b and the chromel wire 9b forms a differential thermocouple of chromel-constantan-chromel and, between the chromel wire 9a and the chromel wire 9b, there is outputted a thermal electromotive force corresponding to a temperature difference between the sample holder 5a and the reference material holder 5b, which correspond to junction points, and it is converted into the differential heat flow signal through a suitable amplifier. On the other hand, the chromel wire 9a and the alumel wire 10a form a thermocouple in the back face of the sample holder 5a, and output a temperature of the sample holder 5a through a cold contact point circuit and a thermal electromotive force/temperature alteration circuit, which are not shown in the drawing.

Next, operations in this embodiment are explained. A measuring person installs a sample container (not shown in the drawing) in which the sample to be measured is stuffed and a reference material container (not shown in the drawing) in which the reference material, whose thermal stability in a temperature range to be measured is confirmed, is stuffed, to the sample holder 5a and the reference material holder Sb. Thereafter, if a start of the measurement is instructed, the heater 20 controls the temperature of the heat reservoir 1 in accordance with a temperature program. At this time, a heat inflow from the heat reservoir 1 to the sensor plate 4 flows, as shown by a heat flow 7 in FIG. 2, from a cylindrical part of the heat reservoir 1 to the sensor plate 4 through the bottom plate part and the protrusion part 2 near a bottom plate part center. By this, the protrusion part 2 becomes the neck-like part of the heat flow passage, the temperature distribution in an X-X' direction in the bottom plate part is reduced, and the heat flow flowing to the sensor plate 4 becomes stable one.

On the other hand, the heat flows flowing-in through the protrusion part 2 pass respectively the two-dimension heat flow paths 4a, 4b from the semicircular arc parts 2a, 2b as shown by heat flows 8 in FIG. 3, and enter to the sample holder 5a and the reference material holder 5b. By this, the heat flows conduct to the sample in the sample container and the reference material, which are mounted on the respective holders. If a thermal change, such as phase transition of the sample, appears, a temperature of the sample holder 5a changes, and a heat flow compensation is performed by the heat flows 8 shown in FIG. 3 through the two-dimension heat path 4a in a sample side. In the embodiment, with a holder diameter 5 mm and semicircular arc part diameter 9 mm, there is obtained the heat compensation time constant of about 2 seconds. This time constant is a rapidness equivalent to an input compensation type differential scanning calorimeter.

In the present embodiment, although there is explained with the structure in which the presser plate 3 nips the sensor plate 4, and is fixed to the protrusion part 2 by the screws 6, it is self-evident that similar advantages are obtained also by other fixation method such as brazing. Further, in the present embodiment, although there is explained with the structure in which the protrusion part 2 has the semicircular arc parts 2a, 2b, as seen in a different embodiment shown in FIG. 4, also with a protrusion part 22 of a longitudinally long structure and a sensor plate of a quadrangular shape like a sensor plate 24, it is self-evident that the protrusion part 22 becomes the neck-like part of the heat flow passage and the stability can be ensured, and the heat flow paths to the holders 5a, 5b form the two-dimension heat flow passages and thus excel in a heat compensation responsiveness, so that the similar advantages are obtained.

The invention claimed is:

1. A heat flow flux type differential scanning calorimeter comprising:
   a heat reservoir configured to supply heat;
   a thermally conductive joint having opposite two ends, one end thereof constituting a heat inflow portion being in contact with the heat reservoir such that the joint receives heat from the heat reservoir via the heat inflow portion, and the other end thereof constituting a heat outflow portion being isolated from the heat reservoir and having two arcuate cutouts formed therein;
   a sensor plate being in contact with the heat outflow portion of the thermal joint except two peripheral portions surrounded by the two arcuate cutouts of the heat outflow portion, such that the two peripheral portions receive heat from the heat outflow portion through multiple heat flow paths in multiple directions extending from the arcuate cutouts of the heat outflow portion; and
   a sample holder and a reference material holder formed in the peripheral portions.

2. A heat flow flux type differential scanning calorimeter according to claim 1, wherein the heat reservoir is made of silver.

3. A heat flow flux type differential scanning calorimeter according to claim 1, wherein the two arcuate cutouts are identical to each other.

4. A heat flow flux type differential scanning calorimeter according to claim 1, wherein the sensor plate is substantially oval in its shape.

5. A heat flow flux type differential scanning calorimeter according to claim 1, wherein the sample holder and the reference material holder are formed as platforms.

6. A heat flow flux type differential scanning calorimeter according to claim 1, wherein the sample holder and the reference material holder each comprise a disk made of a material selected from the group consisting of gold, platinum and silver.

7. A heat flow flux type differential scanning calorimeter-according to claim 1, wherein the arcuate contours of the heat outflow portion defined by each delineate a part of a circle along a contact with the sensor plate within the range between ¼ and ½ of the circle.

8. A heat flow flux type differential scanning calorimeter-according to claim 1, wherein the sensor plate is made of a metal having a thermal conductivity lower than silver.

9. A heat flow flux type differential scanning calorimeter according to claim 8, wherein the sensor plate is made of constantan.

10. A heat flow flux type differential scanning calorimeter according to claim 1, wherein the heat outflow portion of the thermal joint comprises an upper part and a lower part between which the sensor plate is held.

11. A heat flow flux type differential scanning calorimeter according to claim 6, wherein the upper part and the lower part have surfaces of an identical shape which hold the sensor plate therebetween.

12. A heat flow flux type differential scanning calorimeter according to claim 6, wherein the upper part is made of silver.

* * * * *